United States Patent [19]

Steiner

[11] 4,116,936

[45] Sep. 26, 1978

[54] POLYVINYLBENZYL ETHERS OF POLYPHENOLS, THEIR POLYMERS AND COPOLYMERS

[75] Inventor: Edwin C. Steiner, Midland, Mich.

[73] Assignee: The Dow Chemical Company, Midland, Mich.

[21] Appl. No.: 720,923

[22] Filed: Sep. 7, 1976

Related U.S. Application Data

[63] Continuation-in-part of Ser. No. 598,528, Jul. 23, 1975, abandoned.

[51] Int. Cl.$^2$ .................... C08F 36/00; C08F 12/34; C08F 28/04
[52] U.S. Cl. .................... 526/286; 526/288; 526/292; 526/293; 526/313
[58] Field of Search .......... 260/47 UA, 49, 79.3 MU, 260/79.5 R, 59 R, 79.7, 607 A, 607 B, 612 R, 612 D, 613 R

[56] References Cited

U.S. PATENT DOCUMENTS

| | | | |
|---|---|---|---|
| 2,233,080 | 2/1941 | Hester et al. | 260/47 UA |
| 2,522,501 | 9/1950 | Brooks et al. | 260/47 UA |
| 3,663,625 | 5/1972 | Neville | 260/612 R |

*Primary Examiner*—Joseph L. Schofer
*Assistant Examiner*—Peter Kulkosky

[57] ABSTRACT

Vinylbenzyl ethers of polyphenolics such as bisphenol A and novolac resins comprise a new class of curable resins which have marked advantages over comparable types of resins. They have the greater ease of free-radical curing compared to epoxy resins. The cured resins have greater stability than polyester resins because of the lack of hydrolyzable groups, and they have high heat distortion temperatures. Additionally, the resins produce solutions of low viscosity with comonomers such as styrene.

8 Claims, No Drawings

POLYVINYLBENZYL ETHERS OF POLYPHENOLS, THEIR POLYMERS AND COPOLYMERS

REFERENCE TO COPENDING APPLICATION

This application is a continuation-in-part of U.S. Ser. No. 598,528 filed July 23, 1975 and now abandoned.

BACKGROUND

To take advantage of the beneficial properties of polyepoxides and to produce thermosettable resins superior to unsaturated polyesters a new commercial line of resins has been developed based on the reaction of a vinyl acid such as acrylic acid with a polyepoxide. The resins are readily cured by free radical means such as exposure to radiation or to chemical initiators. However, for some purposes, these resins do not have high enough heat distortion properties, are sometimes too viscous in monomer solutions or are not as resistant to water or hydrolysis conditions as desired. Since the reaction of an acid with an epoxide produces a hydroxy alkyl ester linkage these deficiencies are believed to be due to either the ester group or the hydroxyl group or both.

Diallyl ethers of dihydroxy diphenyls (U.S. Pat. No. 2,227,805) and of bisphenol A (U.S. Pat. Nos. 2,560,350 and 3,060,243) have been prepared. The former were taught to be useful as plasticizing or modifying agents and as intermediates for preparing dyes, etc. The latter were taught to be useful as a miticide. However, the allyl group does not polymerize as readily as other unsaturated groups.

Various vinyl derivatives of diphenyl oxide are disclosed in U.S. Pat. No. 3,663,625 which are cured by means of heat and a Lewis acid to produce polyindanyl polymers. To introduce ultraviolet light absorbing groups into polymeric materials to stabilize them against exposure to light U.S. Pat. Nos. 3,049,503 and 3,072,585 disclose vinylbenzyl ethers of benzophenones and phenylbenzotriazoles. None of the beneficial properties obtainable from this invention are disclosed in the above prior art.

SUMMARY OF THE INVENTION

Beneficially the polyvinylbenzyl ethers of this invention in the polymerized state provide better stability and resistance to water and hydrolysis conditions by elimination of both the terminal ester group and alkylhydroxy group found in prior art resins. Other properties are also improved such as corrosion resistance and heat distortion. Handling properties because of lower viscosities of resin/monomer solutions are also improved.

The various polyvinylbenzyl ethers are prepared from various polyhydric phenols such as bisphenol A, from novolac resins, mononuclear phenols and other polynuclear phenols. The phenolic backbones provide many beneficial properties similar to epoxy resins which are prepared from like phenolic compounds.

DESCRIPTION

More specifically, the polyvinylbenzyl ethers of this invention may be defined by the following formulas:

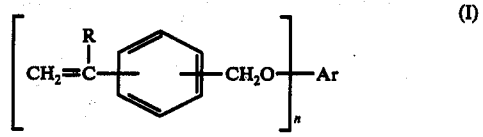

wherein Ar is a radical of an aromatic nucleus such as —$C_6H_4$—, —$C_6H_4$—$C_6H_4$—, —$C_{10}H_6$—, —$C_6H_4$—$CH_2$—$C_6H_4$—, —$C_{10}H_6$—$CH_2$—$C_{10}H_6$— or

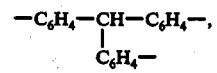

R is hydrogen or methyl and n is 2 or 3.

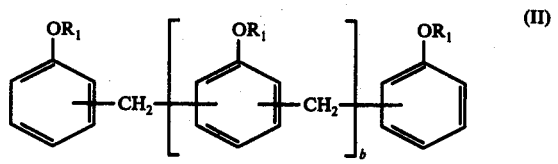

$R_1$ has the formula

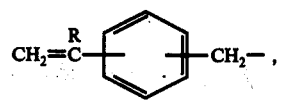

R is hydrogen or methyl and b has an average value from 0.2 to 2.5.

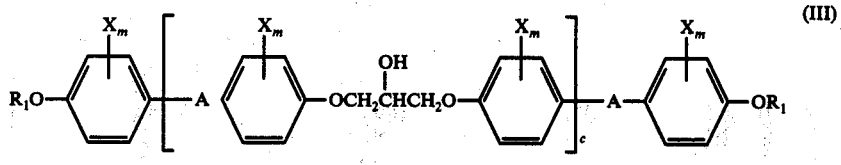

$R_1$ is the same as in formula II. X is an inert substituent such as alkyl, alkoxy, phenyl or halogen and m may be 0, 1 or 2. The group A may be any of the following linking groups: —O—, —S—, —SO— or —$CR_2R_3$—, where $R_2$ and $R_3$ each may be hydrogen or a lower alkyl and c has an average value from 0 up to about 20.

The following non-limiting examples will further illustrate the invention.

EXAMPLE 1

Bisphenol A (228 grams, 1 mol) and vinylbenzyl chloride (336 grams, 2.20 mol of a 60:40 mixture of meta and para isomers, respectively) were dissolved in 500 ml of acetone. The solution was heated to reflux and a solution of 136 grams of KOH (86%) in 300 ml of methanol was added over a period of 30 minutes. The mixture was refluxed for an additional hour. An additional 500 ml of acetone was added and the solution filtered to remove the precipitated KCl (153 gms, 98%). After adding 0.5 gram hydroquinone the solution was evaporated to dryness on a rotating evaporator at 70° C. The residual oil was poured with rapid stirring into 2 liters of methanol to precipitate a granular white solid. After drying in vacuo at 50° C. for 2 hours a product yield of 434 grams (94%) was obtained.

A 40 gram sample of the off-white product was recrystallized to yield 36 grams of colorless platelets which were analyzed for carbon and hydrogen.

|   | Calc. | Found |
|---|---|---|
| C | 86.4 | 86.6, 86.9 |
| H | 6.77 | 7.02, 6.95 |

Nmr analysis confirmed the structure to be the bis(vinylbenzyl) ether of bisphenol A.

EXAMPLE 2

In a similar manner bisphenol S (Formula III where A is $-SO_2-$, $c$ is zero and $m$ is zero) was reacted with vinylbenzyl chloride in the presence of KOH. The product was recovered by evaporating to dryness and redissolving in chloroform. The chloroform solution was extracted with water to remove the salt. Then it was evaporated to dryness and triturated with methanol to yield a soft white powder. The powder was recrystallized from a 1:1 mixture of ethanol and benzene. A total yield of 290 grams of fine white crystals with a m.p. of 158° C. was obtained. A sample for analysis was recrystallized three times.

|   | Calc. | Found |
|---|---|---|
| C | 74.7 | 74.6 |
| H | 5.43 | 5.44 |
| S | 6.64 | 7.00 |

The structure was confirmed by Nmr analysis as the bis(vinylbenzyl) ether of bisphenol S.

EXAMPLE 3

A polyhydric phenol of higher molecular weight than bisphenol A was prepared by reacting 2.31 mols of bisphenol A with 1 mol of a diglycidyl ether of bisphenol A at 200° C. for about 2 hours in the presence of 4.3 grams of triphenylphosphine catalyst. The melt was poured onto an aluminum sheet to cool to a friable glass. A portion of this glass (400 grams, 0.6 mol calc.) was dissolved in 400 ml of t-butyl alcohol and 400 ml of benzene along with 220 grams (1.44 mol) of vinylbenzyl chloride and 0.5 gram of hydroquinone. Over a period of 45 minutes, under nitrogen, at 70° C. aqueous KOH (1.32 mol) was added dropwise. The mixture was then stirred at 70° C. an additional hour. The precipitated KCl was filtered off and the filtrate evaporated at 90° C. and 1 mm pressure. The residual oil was triturated once with boiling methanol and twice with methanol at room temperature, the supernate being decanted each time. The residue was evaporated again to yield 400 grams of product (74% yield). Thin layer chromatography (silica gel, 1% ethanol in $CHCl_3$) indicated most of the phenolic material had been removed. This was confirmed by analysis

| $-C=C-$ | 2.42 mmol/gram |
|---|---|
| ArOH | 0.26 meq/gram |

EXAMPLE 4

In a similar manner bisphenol S (250 grams, 1 mol) was reacted with 0.67 mol of the diglycidyl ether of bisphenol A. The condensate (200 gram, 0.18 mol) was dissolved in 300 ml of boiling acetone along with 67 grams (0.44 mol) of vinylbenzyl chloride. t-Butyl alcohol (150 ml) was added slowly along with 0.3 gram of hydroquinone. Aqueous KOH (0.4 mol) was added over several hours at reflux and refluxing continued for a total of 13 hours. Because the product was not completely soluble the mixture was filtered hot and the solids washed three times with boiling acetone. The washings were evaporated under slight vacuum at 80° C. until most of the solvent was removed. The vacuum was then increased and the product foamed into a friable mass which could be crushed and dried further.

| $-C=C-$ | 1.62 mmol/gram |
|---|---|
| ArOH | 0.06 meq/gram |

EXAMPLE 5

Each of the polyvinylbenzyl ethers of the previous examples were readily polymerized to tough, horny resins when heated with about 1% of benzoyl peroxide, t-butyl peroxide or other suitable radical initiators.

EXAMPLE 6

Equal parts of styrene and the polyvinylbenzyl ether of example 1 were blended and 1% benzoyl peroxide added. The mixture was allowed to polymerize at 80° C. or 13 hours and then at 125° C. or 1 hour. The product was a tough very clear resin. The product of example 2 was copolymerized with styrene in a similar manner with a similar result. The product of Example 3 was dissolved in two parts of styrene and polymerized in a similar manner. A hazy, tough product was obtained. Equal parts of the product of Example 4 and styrene were polymerized in the same manner to produce a clear, horny resin.

The polyvinylbenzyl ethers are thermosettable resins which can be readily polymerized in the presence of free radical initiators and in combination with monomers. In addition the polymerization may be initiated by exposure to ionizing radiation such as gamma rays or accelerated electrons or by exposure to ultraviolet light preferably in combination with a photoinitiator.

Any of a variety of copolymerizable monomers may be employed in any compatible proportions. Alkenyl aromatic monomers such as styrene and including vinyltoluene, α-methyl styrene, various isomers of chlorostyrene and other halogen substituted monomers, t-butyl styrene and like alkyl substituted monomers may be employed. Acrylate and methacrylate esters are another very useful class of monomers. Alkyl, cycloalkyl and hydroxyalkyl esters of acrylic and methacrylic acids are contemplated. Also included are the acrylate and methacrylate esters of polyhydric alcohols, such as the di-, tri- and tetraacrylates of pentaerythritol. Many other commonly known monomers may be employed. The above are meant to be illustrative and not limiting.

Resins such as disclosed herein are useful in making reinforced plastic articles similar to those made from unsaturated polyesters, terminally unsaturated vinyl ester resins and the like. The resins are useful, also, as coating materials, as molding resins, adhesives and in formulating ultraviolet light curable inks and coatings.

It is to be understood that various additives may be combined with these polyvinylbenzyl ester resins for particular purposes dependent on the end use. In addition to photoinitiators and monomers, such materials include inert fillers such as clay, CaCO$_3$, etc.; glass and other fiber reinforcing materials; polymeric additives for low profile or impact resistance, colorants or pigments; mold release agents; etc. The resins may also be combined with other free radical polymerizable resins such as the unsaturated polyesters, etc.

Of particular value in the above, and other, applications are the high heat distortion temperatures obtainable upon polymerization as well as the low viscosity characteristics when combined with such monomers as styrene which is widely used with resins of this kind. The resins are also particularly valuable for their corrosion resistance when polymerized or copolymerized.

EXAMPLE 7

A solution of 55 parts of bis(vinylbenzyl)ether of bisphenol A and 45 parts of styrene was prepared to evaluate the liquid physical properties and to determine the physical, thermal and corrosion resistance properties in the cured state.

Liquid Properties

Gel Time, 1% benzoyl peroxide (BP)

|  | at 180° F (82° C) | at 250° F (121° C) |
|---|---|---|
| Gel time, minutes | 4.57 | 1.23 |
| Peak time, minutes | 8.18 | 2.16 |
| Peak Temp., ° F | 426 | 522 |
| Kinematic Viscosity: 7.10 centistokes | | |

Clear Casting Properties (1% BP)

| Flex Strength, psi | Flex Modulus, psi × 10$^5$ | Tensile psi | HDT, ° F | Elong. % |
|---|---|---|---|---|
| 17,300[1] | 4.6 | 9,880 | 274 (134.4° C) | — |
| 19,081[2] | 4.46 | 7,840 | 292 (144.4° C) | 2.0 |

[1] Cure schedule: 16 hrs. at 80° C and 1 hr. at 250° F (121° C) post cure.
[2] After cure schedule shown under Thermal Properties.

Thermal Properties—Heat Distortion Temperature (HDT)

HDT, 264 psi at increasing post-cure temperatures of clear casting.

| Cycle | Post Cure Conditions | HDT, ° F |
|---|---|---|
| I | 1 hr at 200° F (93.3° C) | 260 (126.7° C) |
| II | Cycle I + 1 hat at 250° F (121° C) | 272 (133.3° C) |
| III | Cycle II + 1 hr at 300° F (148.9° C) | 278 (136.7+ C) |
| IV | Cycle III + 1 hr at 400° F (204.4° C) | 292 (144.4° C) |

Corrosion Test at 98° C.

| Environment | Flex Str. after 12 mos. | % Retention | Flex. Mod. psi × 10$^5$ | % Retention |
|---|---|---|---|---|
| De-ionized Water | 13,650 | 78.7 | 5.2 | 124 |
| 10% NaOH | 16,100 | 92.8 | 5.4 | 128 |
| 32% HCl | 14,200 | 81.8 | 5.5 | 131 |
| none; initial properties | 17,350 |  | 4.2 |  |

The previous results illustrate the numerous advantages of this new class of resins with respect to liquid properties and to physical properties, corrosion resistance and heat distortion temperatures of the polymerized products.

What is claimed is:

1. A thermoset polymeric product obtained by the addition polymerization of an unsaturated monomer having the formula:

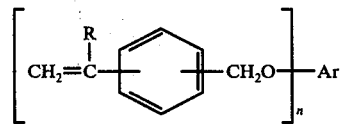

wherein Ar is a radical of an aromatic nucleus selected from the group consisting of —C$_6$H$_4$—; —C$_6$H$_4$—C$_6$H$_4$—; —C$_{10}$H$_6$—; —C$_{10}$H$_6$—CH$_2$—C$_{10}$H$_6$—; —C$_6$H$_2$—CH$_2$—C$_6$H$_4$—; and

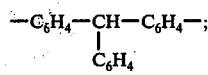

where R is hydrogen or methyl and n is 2 or 3.

2. The polymeric product of claim 1 resulting from the copolymerization of said unsaturated monomer and an ethylenically unsaturated copolymerizable monomer.

3. The polymeric product of claim 1 wherein said unsaturated monomer has the formula:

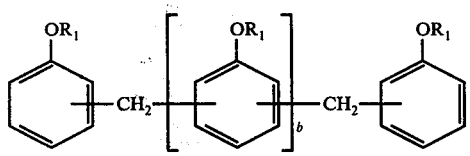

where b has an average value from 0.2 to 2.5 and R$_1$ has the formula:

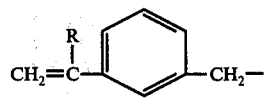

where R is hydrogen or methyl.

4. The polymeric product of claim 1 wherein said unsaturated monomer has the formula:

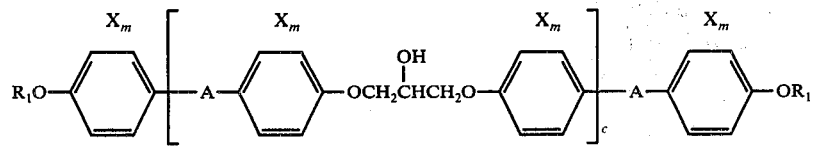

where X is a lower alkyl, alkoxy, phenyl or halogen; $m$ is 0, 1 or 2; $c$ has an average value from 0 up to about 20; A is —O—, —S—, —SO—, —SO$_2$— or —CR$_2$R$_3$—; R$_2$ and R$_3$ each may be hydrogen or a lower alkyl; and R$_1$ has the formula:

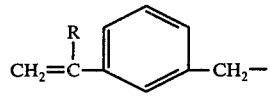

where R is hydrogen or methyl.

5. The polymeric product of claim 4 wherein A is isopropylidene.

6. The polymeric product of claim 4 wherein C is 0.

7. The polymeric product of claim 4 wherein X is chlorine or bromine.

8. The polymeric product of claim 4 wherein R is hydrogen.

* * * * *

UNITED STATES PATENT OFFICE
CERTIFICATE OF CORRECTION

Patent No. 4,116,936  Dated Sept. 26, 1978

Inventor(s) Edwin C. Steiner

It is certified that error appears in the above-identified patent and that said Letters Patent are hereby corrected as shown below:

Column 5, line 65, in the table, third column, delete "(136.7+C)" and insert --(136.7°C)--

Column 6, line 63 - the formula should appear as follows:

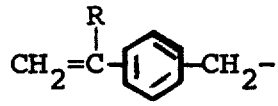

Column 8, line 13 - the formula should appear as follows:

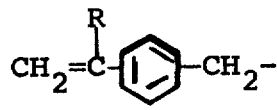

Signed and Sealed this

Twentieth Day of February 1979

[SEAL]

Attest:

RUTH C. MASON
Attesting Officer

DONALD W. BANNER
Commissioner of Patents and Trademarks